United States Patent [19]

Garcia et al.

[11] Patent Number: 4,960,867
[45] Date of Patent: Oct. 2, 1990

[54] LEIURUS QUINQUESTRIATUS VENOM PEPTIDE INHIBITOR OF CALCIUM ACTIVATED POTASSIUM CHANNELS

[75] Inventors: Maria Garcia, Edison; Guillermo Gimenez-Gallego, Jersey City, both of N.J.

[73] Assignee: Merck & Co., Inc., Rahway, N.J.

[21] Appl. No.: 462,898

[22] Filed: Dec. 29, 1989

Related U.S. Application Data

[63] Continuation of Ser. No. 103,323, Oct. 1, 1987, abandoned.

[51] Int. Cl.⁵ .......... C07K 7/10
[52] U.S. Cl. .......... 530/324; 435/29; 436/63
[58] Field of Search .......... 530/324; 435/29; 436/63

[56] References Cited

PUBLICATIONS

Smith C. et al., The Journal of Biological Chemistry, vol. 261, No. 31 pp. 14607–14613 (Nov. 5, 1986).
Miller C. et al., Nature, vol. 313:24 (1985), pp. 316–318.
Goh et al., J. Physiol. (1987), vol. 394, pp. 315–330.
Anderson et al., J. Gen. Physiol., (Mar. 1988), vol. 91, pp. 317–333.
Gimenez-Gallego et al., Proc. Natl. Acad. Sci. U.S.A., (1988), vol. 85, pp. 3329–3333.

*Primary Examiner*—Howard E. Schain
*Assistant Examiner*—Choon Park Koh
*Attorney, Agent, or Firm*—Richard S. Parr; Charles M. Caruso

[57] ABSTRACT

The amino acid sequence:

PYQ-F-T-N-V-S-C-T-T-S-K-E-C-W-S-V-C-Q-R-L-H-N-T-S-R-G-K-C-M-N-K-K-C-R-C-Y-S of charybdotoxin peptide, isolated and purified from the venom of the scorpion *Leiurus quinquestriatus hebraeus,* which peptide is a specific probe for a high-conductance calcium-activated potassium channel found in the plasma membrane of a variety of electrically-excitable tissues.

1 Claim, No Drawings

LEIURUS QUINQUESTRIATUS VENOM PEPTIDE INHIBITOR OF CALCIUM ACTIVATED POTASSIUM CHANNELS

This is a continuation of application Ser. No. 103,323 filed Oct. 1, 1987, now abandoned.

The present invention is concerned with the purification and amino acid sequence of charybdotoxin peptide, which is isolated and purified from the venom of the scorpion *Leiurus quinquestriatus hebraeus* and is useful as a specific probe for calcium ($Ca^{2+}$)-activated potassium ($K^+$) channels or to assess the pharmacological properties of $Ca^{2+}$-activated $K^+$ channels. Used in this fashion, it is an effective ligand to aid in purifying $Ca^{2+}$-activated $K^+$ channels and in establishing biochemical assays based on ligand binding protocols with which to screen for other novel modulators of channel activity.

BACKGROUND OF THE INVENTION

The Israeli scorpion *Leiurus quinquestriatus hebraeus* produces a venom which is known to inhibit a number of different potassium ($K^+$) channel pathways in vertebrates. These include two different classes of calcium ($Ca^{2+}$)-activated $K^+$ channels that are inhibited by different venom components: an apamin-sensitive $Ca^{2+}$-activated $K^+$ channel, such as that found in guinea pig hepatocytes; and an apamin-insensitive $Ca^{2+}$-activated $K^+$ channel, such as found, for example, in human erythrocytes, Ehrlich cells and rat thymocytes (Abia, A., et al., *Biochem. Biophys. Acta.*, 856, 403 (1986), Castle, N. A., and Strong, P. N., *FEBS Lett.* 209, 117 (1986))

Of the many constituents present in the scorpion's crude venom, one minor component is a toxin (called charybdotoxin) that has been shown to block reversibly a $Ca^{2+}$-activated $K^+$ channel isolated from rat skeletal muscle and reconstituted into planar lipid bilayers (Miller et al., *Nature*, 313, 316 (1985)). Charybdotoxin (ChTX), appears to be a small molecular weight basic protein that only inhibits channel activity when added at the external face of the channel protein. An initial report on ChTX confirmed this protein to be a high affinity selective inhibitor of the high conductance (ca. 200 picosemens; 200 pS) $Ca^{2+}$-activated $K^+$ channel found in the plasma membrane of many vertebrate cells (Smith, C., et al , *J. Biol. Chem.* 261, 14607 (1986)).

Smith et al. in *J. Biol Chem.* also included a characterization of the physical and chemical properties of the toxin, wherein ChTX was reported to have an apparent molecular weight of approximately 10 KDa, to be unusually stable to organic solvents or heat treatment, and to inhibit $Ca^{2+}$- activated $K^+$ channel function with an apparent dissociation constant of 3.5 nM. Subsequently, ChTX was also found to inhibit low conductance (ca. 35 pS) $Ca^{2+}$-activated $K^+$ channels in neurons from the marine mollusk *Aplysia californica*, but not block sodium ($Na^+$), $Ca^{2+}$, transient $K^+$ or delayed rectifying $K^+$ channels in this preparation (Herman, A., and Erxleben, C., *J. Gen. Physiol.* 90, 27, (1987)).

ChTX, therefore, represents the only described agent known to cause potent specific inhibition of the apamin insensitive class of $Ca^{2+}$-activated $K^+$ channels. However, to be a useful probe for these channels, ChTX must be purified to homogeneity from the crude venom, which contains many different activities, and its structure must be correctly elucidated.

The present invention discloses for the first time the purification of ChTX to homogeneity, the chemical structure of this peptide, and the biological activity of the pure toxin, which had been previously mischaracterized by Smith et al. in terms of its purity, molecular weight, amino acid composition and N-terminal amino acid residue.

DESCRIPTION OF THE INVENTION

The present invention provides a bioactive peptide, called charybdotoxin (ChTX), of the formula:

which is a naturally occurring protein in the venom of the scorpion *Leiurus quinquestriatus hebreaus*, having a 4.3 KDa molecular weight.

All abbreviations used herein and not otherwise identified are standard abbreviations approved for publication in the *Journal of Biological Chemistry* (all amino acids are in the L-configuration). These amino acid residue abbreviations include:

| Abbreviated Designation | Amino Acid Residue |
|---|---|
| C | Cysteine |
| E | Glutamic Acid |
| F | Phenylalanine |
| G | Glycine |
| H | Histidine |
| K | Lysine |
| L | Leucine |
| M | Methionine |
| N | Asparagine |
| PYQ | Pyroglutamine |
| Q | Glutamine |
| R | Arginine |
| S | Serine |
| T | Threonine |
| V | Valine |
| W | Tryptophan |
| Y | Tyrosine |

ChTX is a selective and very potent, reversible inhibitor of the high conductance calcium ($Ca^{2+}$) activated potassium ($K^+$) channel found in many electrically-excitable cells, such as bovine aortic smooth muscle and $GH_3$ rat anterior pituitary cells. It functions by blocking the external pore of the channel, binding at this site with nM affinity. By inhibiting this channel, ChTX promotes contraction of rat portal vein.

Because of its selectivity and potency, this toxin is useful as a probe for $Ca^{2+}$-activated $K^+$ channel function in a variety of tissues, thereby allowing it to be used for investigating the pharmacology of this $K^+$ channel in different tissues, aiding in the purification of $Ca^{2+}$-activated $K^+$ channels from different tissue sources, and establishing ligand binding assays to probe for other novel modulators of $Ca^{2+}$-activated $K^+$ channel activity.

A peptide with ChTX activity was purified from the venom of *Leiurus quinquestriatus hebraeus*, a commercially available lyophilized scorpion venom, taking advantage of the highly basic nature of the protein. In the purification procedure, the toxin was isolated by successive cation exchange and reverse phase high performance liquid chromatographies, and was considered homogeneous based on chromatographic and electrophoretic criteria. Typically, processing of 100 mg of the crude lyophilized scorpion venom yields 200–300 μg of the pure toxin.

The amino acid composition and sequence of ChTX, based upon data described in the Examples, indicate that the protein contains seven basic but only one acidic residue among its 37 amino acid moieties and lacks aspartic acid, alanine, proline and isoleucine residues. The fact that one of the glutamic residues is in the form of a pyroglutamine at the N-terminus of ChTX indicates why it is not possible to apply directly the sequential Edman degradation technique to determine the primary structure of this protein. When considered together, these factors distinguish the actual ChTX from the protein characterized in the Smith et al. reference.

The sequence of the complete 37-amino acid residue ChTX peptide was established by determining sequences of overlapping peptides. These overlapping peptides were generated by cleavage of ChTX with either endoproteinase Lys-C, *Staphilococcus aureus* V-8 protease, or pyroglutamate aminopeptidase using conventional procedures.

Treatment with pyroglutamate aminopeptidase unblocks the N terminal of the protein allowing the primary structure of the remaining 36-amino acid residue peptide to be determined by sequential Edman degradation. Then, the carboxyl terminus of ChTX was confirmed by timed digestion of the whole protein with carboxypeptidase A. The sequencing strategy is outlined below, resulting in the sequence:

PYQ-F-T-N-V-S-C-T-T-S-K-E-C-W-S-V-C-Q-R-L-H-N-T-S-R-G-K-C-M-N-K-K-C-R-C-Y-S

```
                            PQase
    ─────────────────────────────────────────────────────>
    V8 #132 - HCl           V8 #138
    ─────────────────>      ─────────────────────────────>
    E-LYS C - HCl #14a   E-LYS C #19   E-LYS C #2   E-LYS C #9
    ─────────────────>   ──────────>   ──────────>  ──────────>
        14b
    ──────>
        14c
    ──────>
        14d
    ──────>
                                                        CPA
                                                    <──────
``` where PQase is the sequence of the peptide that results from pyroglutamate aminopeptidase treatment; V8#138 is the sequence of a peptide that results from *Staphilococcus aureus* V-8 protease treatment; V8#132-HCl is the sequence of another peptide derived from *Staphilococcus aureus* cleavage and later subjected to limited hydrolysis with HCl; E-LYSC #2, #9, and #19 are sequences of peptides derived from endoproteinase lysine-C treatment; E-LYS-HCl #14 a–d are peptide sequences generated after endoproteinase lysine-C treatment, followed by limited hydrolysis with HCl; and CPA is the sequence inferred from the timed digestion of ChTX with carboxypeptidase A.

The biological activity of ChTX in either crude venom, or in partially purified or homogeneous protein fractions was ascertained by electrical analysis of single high conductance $Ca^{2+}$ activated $K^+$ channels in isolated plasma membrane patches derived from either aortic smooth muscle or pituitary cells possessing this activity. Measurements were accomplished using patch clamp techniques (Hamil, O. P., et al., *Pflugers Arch.*, 391, 85 (1981)), with excised patches of membranes oriented with an outside-facing-out polarity, which polarity was confirmed by demonstrating that channel activity responded properly to changes in potential across the membrane (i.e., the frequency and amplitude of channel openings increase with increasingly positive holding potentials). This polarity was also confirmed when 1 to 3 mM tetraethylammonium ion (which only inhibits $Ca^{2+}$-activated $K^+$ channels by interacting at the external pore) promoted rapid reversible block of channel activity.

Inhibition of the 220 pS $Ca^{2+}$-activated $K^+$ channel by ChTX results in an increase in silent periods between bursts of channel activity, as has previously been described with reconstituted $Ca^{2+}$-activated $K^+$ channels from skeletal muscle (Miller et al., (1985), supra. Therefore, exposure to increasing concentrations of the toxin results in a situation where channel openings are greatly suppressed. This characteristic behavior can then also be used to follow ChTX activity during purification procedures.

Analysis of the action of purified ChTX at the single channel level reveals that the toxin blocks the high conductance $Ca^{2+}$-activated $K^+$ channel with an inhibition constant ($K_i$) of 2.1 nM, functioning by binding only at the external face of the channel. It increases the off-time of the channel without affecting mean channel conductance or modifying the individual channel open times. In addition, purified ChTX had no effect on either rapid-inactivating or slowly-inactivating $Ca^{2+}$ currents or on rapid-inactivating $K^+$ currents in GH3 cells, indicating specificity of action of the toxin.

Because $Ca^{2+}$-activated $K^+$ channels have been postulated to control the electrical activity of rat portal vein, and hence modulate muscle contractility (Inoue, R., Kitamura, K. and Kuriyama, H., *Pflugers Arch.* 405, 173 (1985); Inoue, R., Okabe, K., Kitamura, K. and Kuriyama, H., *Pflugers Arch.*. 406, 132 (1986)), it is expected that ChTX would have significant biological activity in this system. Consistent with this hypothesis, ChTX produces a does-dependent contracture of isolated portal vein with an $IC_{50}$ of 10 nM. Taken together, these results indicate that ChTX is a selective high affinity probe for the $Ca^{2+}$-activated $K^+$ channel.

The Examples which follow demonstrate purification of ChTX to homogeneity, determination of the amino acid sequence of this peptide, and demonstration of the biological activity and mode of action of ChTX. They are intended to be representative and not limiting.

EXAMPLE 1

Purification of Charybdotoxin Peptide (ChTX)

Lyophilized *Leiurus quinquestriatus hebraeus* scorpion venom (80 mg, Latoxan Scorpion Farm, Rosans, France) was resuspended in 20 ml of 20 mM sodium borate, pH 9.0 at 4° C., with the resulting mucoid suspension being homogenized by agitation on a vortex mixer (5-10 sec). After repeated passage through the orifice of a glass pipette, the venom suspension was subjected to centrifugation (27 Kg) for 15 min, with the supernatant being retained and the pellet of insoluble debris being discarded. The soluble fraction of the crude venom was then passed twice through Millex-GV 0.2 μm low protein binding filters (Millipore Corp., Bedford, Mass.) in order to prepare the extract for column chromatography.

The entire extract was loaded at a flow rate of 0.5 ml/min, onto a Mono S cation exchange column (HR 5/5, Pharmacia, Piscataway, N.J.), which had been preequilibrated with 20 mM sodium borate, pH 9.0. During this chromatographic step, the 280 nm optical absorption of the eluate was continuously monitored with an on-line detector, although most of the extracted material absorbing at this wavelength was not retained by the column, and displayed no ChTX activity, according to the biological monitoring employed throughout the purification procedure (Example 3).

Once the optical absorption of the eluate decreased to a steady value (within 0.06 optical density units above that of the elution buffer originally), the retained material was eluted with a linear gradient of from 0-to-1.5M sodium chloride over 120 min at room temperature, at a flow rate of 0.5 ml/min. Peaks were manually collected and assayed for ChTX activity, with the bulk of the activity being eluted as a single peak at 0.34M sodium chloride. Protein fractions displaying this activity were stable after being frozen at $-80°$ C.

Fractions containing ChTX activity were loaded onto a reverse phase chromatography column (VYDAC $C_{18}$ column [330 Å pore size, 5 μm particle size, 4.6 mm×25 cm, The Separations Group, Hesperia, Calif.], although an RPSC ultrapore $C_3$ column [330 Å pore size, 5 μm particle size, 4.6 mm ×7.5 cm, Beckman, San Ramon, Calif.] may also be used) equilibrated with 10 mM trifluoroacetic acid and eluted with a 0-20% linear gradient of isopropyl alcohol and acetonitrile (2:1), over a 30 min period at room temperature and at a flow rate of 0.5 ml/min. A major peak with absorbance at 280 nm, and the only one with ChTX activity, eluted at approximately 10% of the gradient. For activity analysis, the samples were made either 350 mM in sodium chloride or 0.5% in bovine serum albumin, lyophilized by vacuum centrifugation and reconstituted to their original volume with 20 mM sodium borate, pH 9. The lyophilized and reconstituted samples were stored at $-80°$ C. without apparent loss of activity.

The peptide from the reverse phase chromatography step was subjected to an electrophoretic analysis, using a Mini Protein II Dual Slab Cell (Bio-Rad, Richmond, Calif.) with a 1.6 mm thick, 25.7% polyacrylamide gel (acrylamide to bisacrylamide ratio 37:1), cast without stacking gel, containing 750 mM Tris•HCL, pH 8.85 and 0.1% SDS. The electrode buffer composition was 50 mM Tris•HCl, pH 8.5, 190 mM glycine, 19 mM thioglycolate and 0.1% SDS, and the samples (375 ng per lane) were treated as described for reducing gels (Thomas, K. A., et al., *Proc. Natl. Acad. Sci. U.S.A.* 81, 357 (1984)). The gel was run for 24 hours at a constant voltage of 3.3 volts per cm of gel.

For visualization purposes, silver staining was employed. The protein was fixed in the gel, as described (Morrissey, J. H., *Anal. Biochem.* 117, 307 (1981)) except that the first two steps were for two hours each, with a change of solution after 60 min in each case, and that the glutaraldehyde treatment was also carried out for two hours. The remainder of the staining procedure was carried out as described in Wray et al., *Anal. Biochem.* 118, 197 (1981), with the gel being overstained and the background later being reduced.

According to the chromatographic profile of, electrophoretic analysis of, and data from the amino acid composition, N-terminal amino acid analysis and amino acid sequence (presented in Example 2), ChTX from the reverse phase chromatography column was judged to be in pure form.

EXAMPLE 2

Amino Acid Composition and Sequence Determination of Charybdotoxin Peptide

A sample (4 μg) of the homogeneous protein obtained in Example 1 was subjected to gas phase hydrolysis in a pico-tag work station (Waters Corp, Milford, Mass.), then derivatized with phenylisothiocyanate to yield phenylthiocarbamyl-amino acids, as described in Bidlingmeyer, B. A., et al., *J. Chromatogr.*, 336, 93 (1984).

The resulting derivatized amino acid mixture was analyzed and quantitated using reverse phase high performance liquid chromatography techniques (Gimenez-Gallego, G., and Thomas, K. A., *J. Chromatogr.*, in press). This analysis yielded the following results:

TABLE I

| AMINO ACID | AMINO ACIDS (SEQUENCE) | AMINO ACIDS (ANALYSIS) |
|---|---|---|
| B | 3 | 3 |
| Z | 3 | 3 |
| S | 5 | 5 |
| G | 1 | 1 |
| H | 1 | 1 |
| R | 3 | 3 |
| T | 4 | 4 |
| Y | 1 | 1 |
| V | 2 | 2 |
| M | 1 | 1 |
| C | 6 | 6 |
| L | 1 | 1 |
| F | 1 | 1 |
| K | 4 | 4 |
| W | 1 | — | where B is Aspartic acid or Asparagine, Z is Glutamic Acid or Glutamine, S is Serine, G is Glycine, H is Histidine, R is Arginine, T is Threonine, Y is Tyrosine, V is Valine, M is Methionine, C is Cysteine, L is Leucine, F is Phenylalanine, K is Lysine and W is Tryptophan.

The cysteine residues of ChTX (250 μg) were subjected to alkylation with iodoacetate, by known procedures (Gimenez-Gallego, G., et al., *Biochem. Biophys. Res. Commun.*, 38, 611 (1986)), and the protein or peptide fragments derived from ChTX were sequenced in an Applied Biosystems 470A microsequencer (Foster City, Calif.) using Polybrene-coated glass fiber filters. Amino acids were detected with an on-line Phenylthiohydantoin-amino acid analyzer (Applied Biosystems model 120A, Foster City, Calif.).

A series of peptides were prepared from ChTX by digesting two aliquots of carboxymethylated ChTX (25 μg) with either endoproteinase Lys-C or *Staphilococcus aureus* V-8 protease, respectively. Before the digestion, ChTX was dried by vacuum centrifugation in glass vials (Kimax 6×50 mm, Kimble, Toledo, Ohio).

For Endoproteinase Lys-C digestion, ChTX was solubilized in 90 μl of 20 mM sodium phosphate, pH 7.6 and then 0.3 units of enzyme (Boehringer Mannheim, Indianapolis, Ind.) in 10 μof the same buffer was added.

The reaction mixture was kept at 37° C. for 24 hours and the peptides resulting from digestion of ChTX were purified by gradient elution from a VYDAC $C_{18}$ column (330 Å pore size, 5 μm particle size, 4.6 mm×25 cm; The Separations Group, Hesperia, Calif.) by reverse phase high performance liquid chromatographic procedures, as described in Thomas, K. A., et al., *Proc. Natl. Acad. Sci. U.S.A.* 82 6409 (1985).

For cleavage at the carboxy terminal side of glutamate residues, ChTX was solubilized in 100 μl of 0.1M ammonium bicarbonate. (BDH AnalaR, Gallard-Schlesinger, Carle Place, N.Y.), pH 7.8 (pH 7.8 minimizes the extent of cleavage of peptide bonds following aspartate residues) and 2 mM EDTA containing 1 μg of *Staphilococcus aureus* V-8 (Miles Laboratories, Elkhart, Ind.). Digestion was performed at 37° C. for 42 hours and the resulting peptides were purified by reverse phase high performance liquid chromatography, as described above for the Endoproteinase Lys-C cleavage products.

Approximately half the amounts of the different peptides generated by either endoproteinase Lys-C or *Staphilococcus aureus* V-8 protease treatment were utilized for sequence determinations.

When no phenylthiohydantoin-amino acid derivatives were detected after three Edman degradation cycles of peptide #132 resulting from the *Staphilococcus aureus* V-8 protease digestion, the sequencer was halted, the glass filter cartridge containing the blocked peptide was disassembled, and an aliquot (30 μl) of 12N hydrochloric acid (Hopkin & Williams UltraR, Chadwell Heath, Essex, England) was applied to the filter disk in situ. The pyrex glass cartridge containing the sample filter disk was placed in a dessicator and left in contact with hydrochloric acid vapor for 30 minutes at 20° C. The glass cartridge containing the sample filter was then vacuum dried for 15 min and air-dried at 44° C. for another 15 min. The cartridqe was reassembled in the sequencer and the sequence analysis was begun again.

The remaining portion of the peptide not loaded in the sequenator, was subjected to hydrolysis with hydrochloric acid and its amino acid composition was determined as described above. Analysis of this composition revealed that the sequence of the peptide lacked two amino acids, phenylalanine and glutamine, suggesting that the blocked amino-terminus of ChTX might be a pyroglutamine residue. Equivalent results were obtained with peptide #14 of the endoproteinase Lys C-digestion, although in this case the hydrolysis of the filter was carried out for 2 hours at room temperature.

To remove the N-terminal pyroglutamate residue, 25 μg of carboxymethylated ChTX was digested with pyroglutamate aminopeptidase (Boehringer Mannheim, Indianapolis, Ind.) as described in Podell N. N. and Abraham G. N., *Biochem. Biophys. Res. Commun.* 81, 176 (1978), except that the total amount of enzyme used for the digestion was added at the beginning of the reaction and the molar ratio between the enzyme and ChTX was adjusted to 1:10.

After the digestion, the reaction mixture was chromatographed by reverse phase high performance liquid chromatography techniques as described above. The results of this chromatography showed essentially a single peak of protein whose amino-terminus was unblocked and whose sequence accounts for the total amino acid composition of ChTX (Table I), except for one glutamic acid residue.

For determination of the C-terminal residue of ChTX, the procedure cf G. Gimenez-Gallego and K. A. Thomas (J. Chromatogr. supra) was followed using 1 nmole of carboxymethylated protein.

EXAMPLE 3

Biological Activity of Charybdotoxin Peptide

Single $Ca^{2+}$-activated $K^+$ channel currents were monitored in excised membrane patches derived from either bovine aortic smooth muscle cells or $GH_3$ anterior pituitary cells.

For these experiments, $GH_3$ cells, obtained from the American Type Culture Collection (Rockville, Md.) were maintained in a medium composed of 50% Dulbecco's modified Eagle medium and 50% Ham's F-10 nutrient mixture to which 15% horse serum and 2.5% fetal calf serum had been added, while primary cultures from bovine aortic smooth muscle were obtained essentially as described in Ross, R., *J. Cell Biol.*, 50, 172 (1971) and cultured in Dulbecco's modified Eagle medium containing 25 mM HEPES, pH 7.3, and supplemented with 15% fetal calf serum. In both cases, cells were grown in a humidified atmosphere containing 5% carbon dioxide at 37° C. For electrophysiological experiments, cells were plated on 25 mm glass cover slips and routinely cultured 2-4 days before use, with these plates being transferred to an experimental chamber which had a volume of 1 ml and which was perfused with bathing medium at a rate of 1 ml/min.

Channel recordings were made by conventional patch clamp procedures as previously described by Hamil, O. P., et al. Using a micromanipulator, a glass micropipette (fabricated from soda lime glass, 5-10 mΩ resistance; containing 150 mM potassium chloride, 2 mM magnesium chloride, 1 5 μM calcium chloride, 10 mM HEPES, pH 7.3) was positioned on the surface of the cell, slight negative pressure was applied and the formation of a high resistance seal between the plasma membrane and pipette was monitored. Seals of $10-50 \times 10^9 \Omega$ were required for subsequent measurements.

After attaining such a seal, the cell membrane was ruptured by application of a rapid negative pressure pulse and the electrode was pulled away from the cell to form an outside-facing-out excised patch at the tip of the electrode. The presence of $Ca^{2+}$-activated $K^+$ channels was then determined, and such activity could be recorded in excised patches for up to two hours. Recordings were made at a holding potential of 0 to +20 mV in a bathing medium consisting of 150 mM sodium chloride, 10 mM HEPES, pH 7.3.

To determine which venom constituents possess the ability to inhibit $Ca^{2+}$-activated $K^+$ channels, aliquots of column fractions were added directly to the experimental chamber and perfusion of the chamber with medium was halted. After recording channel activity for an appropriate length of time, perfusion of the chamber was begun again to washout the added protein.

ChTX block of channel activity, which was fully reversible, was characterized by the appearance of silent periods between bursts of activity. To determine the potency of purified ChTX, recordings were made in which the number of channel events occurring per sec. were measured in the presence of increasing concentrations of toxin. From these experiments, the $K_i$ of ChTX was estimated to be 2.1 nM.

To determine the biological activity of ChTX in isolated rat portal vein, Sprague Dawley rats (250 g) were sacrificed by carbon dioxide asphyxiation their portal veins were quickly removed by surgery, and these tissues were placed in a physiological salt solution (PSS) of the following composition; 130 mM sodium chloride, 4.7 mM potassium chloride, 1.2 mM magnesium chloride, 1.6 mM calcium chloride, 1.2 mM monobasic potassium phosphate, 14.9 mM sodium bicarbonate, 11 mM glucose, and 0.03 mM EDTA, equilibrated with 95% oxygen—5% carbon dioxide at a pH of 7.2. Portal veins were cleaned of extraneous tissue and slit along their longitudinal axis (10–14 mm in length), then tied with surgical thread and secured at one end of a glass hook which was suspended in a jacketed tissue bath (50 ml) containing areated PSS at 38° C.

The venous strips were connected via surgical silk to a Grass force-displacement transducer (FT.03) for monitoring changes in isometric force. Tissues were stretched to approximately 0.75 g of force which allowed for optimal levels of intrinsic phasic contraction to be generated and equilibrated for one hour. Venous segments were washed with fresh PSS every 20 min. during the equilibration period.

After equilibration, the application of ChTX increased the amplitude of the spontaneous, rhythmic contractions of the portal venous strips. A dose-response curve was constructed by adding increasing concentrations of ChTX cumulatively to the tissue bath once a particular level of force reached an equilibrated plateau and contraction was noted as the percent increase in the amplitude of phasic contraction. Under these conditions, purified ChTX increased force development maximally by 50% with an $IC_{50}$ of 10 nM.

What is claimed is:

1. A composition for assessing the contribution of high conductance $Ca^{2+}$-activated $K^+$ channels in smooth muscle comprising a purified peptide of the formula:

PYQ-F-T-N-V-S-T-T-S-K-E-C-W-S-V-C-Q-R-L-H-N-T-S-R-G-K-C-M-N-K-K-C-R-C-Y-S.

* * * * *

UNITED STATES PATENT AND TRADEMARK OFFICE
CERTIFICATE OF CORRECTION

PATENT NO. : 4,960,867
DATED : October 2, 1990
INVENTOR(S) : Maria Garcia and Guillermo Gimenez-Gallego It is certified that error appears in the above-indentified patent and that said Letters Patent is hereby corrected as shown below:

Column 10, lines 20 and 21 should read as follows:

PYQ-F-T-N-V-S-C-T-T-S-K-E-C-W-S-V-C-Q-R-L-H-N-T-S-R-G-K-C-M-N-K-K-C-R-C-Y-S

Signed and Sealed this

Twenty-first Day of March, 1995

*Attest:*

BRUCE LEHMAN

*Attesting Officer*  *Commissioner of Patents and Trademarks*